US012685573B2

(12) United States Patent
Fauth et al.

(10) Patent No.: US 12,685,573 B2
(45) Date of Patent: Jul. 21, 2026

(54) BONE IMPLANTS, SYSTEMS, AND METHODS

(71) Applicant: RTG Scientific, LLC, Austin, TX (US)

(72) Inventors: Andrew Fauth, North Logan, UT (US);
Eric Brown, Austin, TX (US)

(73) Assignee: RTG Scientific, LLC, Austin, TX (US)

( * ) Notice: Subject to any disclaimer, the term of this patent is extended or adjusted under 35 U.S.C. 154(b) by 331 days.

(21) Appl. No.: 18/134,486

(22) Filed: Apr. 13, 2023

(65) Prior Publication Data

US 2023/0329763 A1 Oct. 19, 2023

Related U.S. Application Data

(60) Provisional application No. 63/330,354, filed on Apr. 13, 2022.

(51) Int. Cl.
*A61B 17/86* (2006.01)
*A61B 17/16* (2006.01)
*A61B 17/88* (2006.01)

(52) U.S. Cl.
CPC ...... *A61B 17/8635* (2013.01); *A61B 17/1655* (2013.01); *A61B 17/8805* (2013.01)

(58) Field of Classification Search
CPC ............ A61B 17/8805; A61B 17/1655; A61B 17/8802
See application file for complete search history.

(56) References Cited

U.S. PATENT DOCUMENTS 3,848,276 A 11/1974 Martinez
4,476,861 A * 10/1984 Dimakos ................ A61B 17/92
606/100
4,810,149 A 3/1989 Lee et al.
5,454,811 A * 10/1995 Huebner ............ A61B 17/8645
606/305
5,964,768 A 10/1999 Huebner
(Continued)

FOREIGN PATENT DOCUMENTS

GB 2033755 A 5/1980

OTHER PUBLICATIONS

International Search Report dated Aug. 10, 2023 for corresponding PCT/US2023/020900.
(Continued)

*Primary Examiner* — David W Bates
(74) *Attorney, Agent, or Firm* — David Meibos; Maywood IP Law

(57) ABSTRACT

Systems and methods for coupling a bone implant to a bone augment material may include coupling a bone augment material to a bone of a patient, forming a helical bone thread in the bone augment material, and coupling a bone implant to the helical bone thread formed in the bone augment material. The bone implant may include a shaft having a proximal end, a distal end, and a longitudinal axis. The bone implant may also include a helical thread disposed about the shaft along the longitudinal axis between the proximal end and the distal end of the shaft and the helical thread may include a concave undercut surface. The helical bone thread formed in the bone augment material may include a convex surface shaped to engage the concave undercut surface of the bone implant to couple the bone implant to the bone augment material.

19 Claims, 7 Drawing Sheets

(56) References Cited

U.S. PATENT DOCUMENTS

| | | | |
|---|---|---|---|
| 5,971,985 A * | 10/1999 | Carchidi | A61B 17/8635 |
| | | | 606/53 |
| 6,800,078 B2 | 10/2004 | Reed | |
| 7,537,603 B2 | 5/2009 | Huebner et al. | |
| 8,337,205 B2 | 12/2012 | Reed | |
| 8,602,781 B2 | 12/2013 | Reed | |
| 8,875,399 B2 | 11/2014 | Reed | |
| 9,079,263 B2 * | 7/2015 | Reed | A61B 17/8635 |
| 9,526,547 B2 * | 12/2016 | Reed | A61B 17/864 |
| 9,687,319 B2 * | 6/2017 | Reed | A61C 8/0018 |
| 9,782,209 B2 | 10/2017 | Reed | |
| 9,901,379 B2 | 2/2018 | Reed | |
| 10,022,018 B2 | 7/2018 | Egger et al. | |
| 10,052,004 B2 | 8/2018 | Kim | |
| 10,085,782 B2 | 10/2018 | Reed | |
| 10,265,177 B2 | 4/2019 | Quinn et al. | |
| 10,441,385 B2 | 10/2019 | Reed | |
| 10,639,086 B2 | 5/2020 | Reed | |
| 10,687,877 B2 | 6/2020 | Lavigne et al. | |
| 11,062,014 B1 | 7/2021 | Raman | |
| 11,222,018 B2 | 1/2022 | Chavan | |
| 12,484,938 B2 * | 12/2025 | Yonezawa | A61B 17/8888 |
| 2003/0083662 A1 * | 5/2003 | Middleton | A61B 17/7098 |
| | | | 606/92 |
| 2003/0088248 A1 | 5/2003 | Reed | |
| 2003/0105468 A1 * | 6/2003 | Gorek | A61B 17/8811 |
| | | | 606/92 |
| 2004/0098442 A1 | 5/2004 | Kishore | |
| 2005/0107800 A1 * | 5/2005 | Frankel | A61B 17/1655 |
| | | | 606/92 |
| 2006/0204930 A1 | 9/2006 | Sul | |
| 2007/0074498 A1 | 4/2007 | Schmidt | |
| 2007/0093833 A1 * | 4/2007 | Kuiper | A61F 2/4405 |
| | | | 606/86 A |
| 2007/0162123 A1 * | 7/2007 | Whittaker | A61B 17/0401 |
| | | | 623/13.14 |
| 2007/0233123 A1 | 10/2007 | Ahmad et al. | |
| 2008/0268056 A1 * | 10/2008 | Joshi | C08L 33/26 |
| | | | 514/772.3 |
| 2009/0069852 A1 | 3/2009 | Farris et al. | |
| 2009/0305189 A1 | 12/2009 | Scortecci et al. | |
| 2010/0094358 A1 | 4/2010 | Moore et al. | |
| 2010/0121327 A1 | 5/2010 | Velikov | |
| 2011/0288650 A1 | 11/2011 | Ries et al. | |
| 2013/0253517 A1 | 9/2013 | Mitchell et al. | |
| 2013/0253595 A1 * | 9/2013 | Zucherman | A61B 17/8635 |
| | | | 606/305 |
| 2014/0023990 A1 | 1/2014 | Zadeh | |
| 2014/0056460 A1 | 2/2014 | Barnes | |
| 2014/0058460 A1 | 2/2014 | Reed | |
| 2014/0207233 A1 * | 7/2014 | Steiner | A61B 17/8875 |
| | | | 623/13.14 |
| 2014/0329202 A1 | 11/2014 | Zadeh | |
| 2016/0100870 A1 | 4/2016 | Lavigne | |
| 2017/0035482 A1 * | 2/2017 | Magee | A61B 17/863 |
| 2018/0303529 A1 | 10/2018 | Zastrozna | |
| 2018/0335070 A1 | 11/2018 | May | |
| 2019/0038426 A1 | 2/2019 | Ek | |
| 2019/0105131 A1 | 4/2019 | Barton et al. | |
| 2019/0223917 A1 | 7/2019 | Gray et al. | |
| 2019/0238085 A1 | 8/2019 | Shi | |
| 2019/0358039 A1 | 11/2019 | Ducharme et al. | |
| 2020/0224657 A1 | 7/2020 | Brandt | |
| 2021/0259842 A1 * | 8/2021 | Feng | A61B 17/7001 |
| 2022/0249148 A1 | 8/2022 | Hyer et al. | |

OTHER PUBLICATIONS

International Search Report dated Jul. 5, 2023 for corresponding PCT/US2023/018561.

* cited by examiner

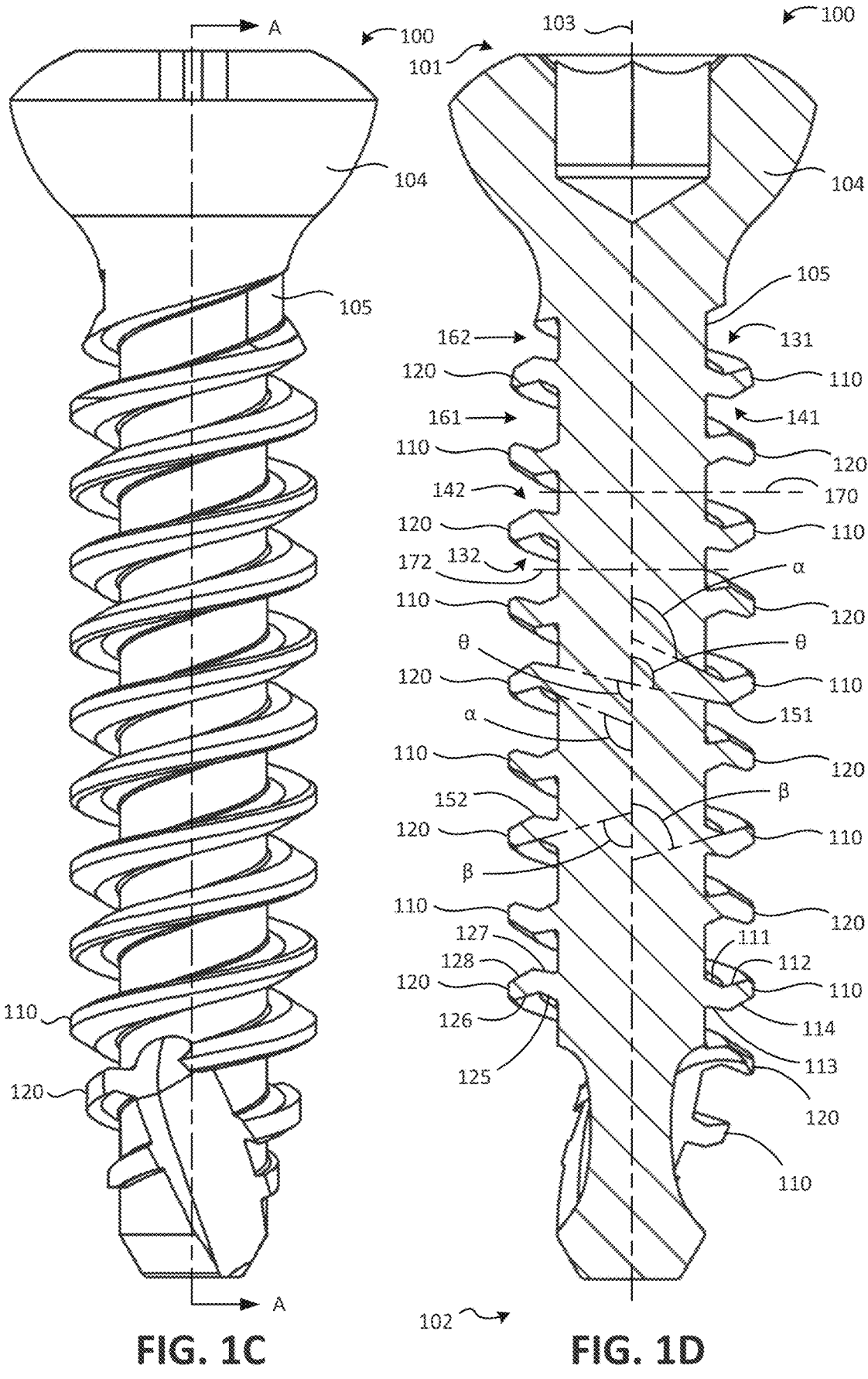
FIG. 1C            FIG. 1D

1

BONE IMPLANTS, SYSTEMS, AND METHODS

CROSS-REFERENCE TO RELATED APPLICATIONS

This application claims the benefit of U.S. Provisional Patent Application Ser. No. 63/330,354 filed on Apr. 13, 2022, entitled "BONE IMPLANTS, SYSTEMS, AND METHODS." The foregoing document is hereby incorporated by reference in its entirety.

TECHNICAL FIELD

The present disclosure relates to bone implants, systems, and methods. More specifically, the present disclosure relates to bone implants, systems, and methods with improved thread designs for coupling with at least one bone augment material.

BACKGROUND

Surgical procedures involving a bone implant coupled within a bone augment material can become lose over time due to degradation of the bone augment material via compression forces, radial outward loading forces, multi-axial forces, and/or off-axis loading scenarios that may be applied to the bone implant/bone augment material interface during the healing process. Traditional thread designs utilizing tapered or wedged shaped surfaces and geometries can produce such undesirable forces and loading scenarios which may lead to degradation of the bone augment material and reduced fixation of the bone implant therein.

Accordingly, bone implants with improved thread designs that can decrease compression and radial outward loading forces, and/or increase fixation and load sharing characteristics between a bone implant/bone augment material interface that experiences multi-axial and off-loading conditions, would be desirable. Such improved thread designs can provide improved fixation, purchase, stability, stiffness, and yield strength, as well as decreased wear and degradation of the bone augment material surrounding the bone implant.

SUMMARY

The various bone implants, systems, and methods of the present disclosure have been developed in response to the present state of the art, and in particular, in response to the problems and needs in the art that have not yet been fully solved by currently available bone implants, systems, and methods. In some embodiments, the bone implants, systems, and methods of the present disclosure may provide improved fixation and load sharing characteristics between a bone implant/bone augment material interface experiencing multi-axial and off-loading conditions.

In some embodiments, a method of coupling a bone implant to a bone augment material may include: coupling a bone augment material to a bone of a patient, forming a helical bone thread in the bone augment material, and coupling a bone implant to the helical bone thread formed in the bone augment material. The bone implant may include a shaft having a proximal end, a distal end, and a longitudinal axis. The bone implant may also include a helical thread disposed about the shaft along the longitudinal axis between the proximal end and the distal end of the shaft and the helical thread may include a concave undercut surface. The helical bone thread formed in the bone augment material

2 may include a convex surface shaped to engage the concave undercut surface of the bone implant to couple the bone implant to the bone augment material.

In some embodiments of the method, the bone augment material may include at least one of: a bone cement, a natural bone graft material, and an artificial bone graft material.

In some embodiments of the method, coupling the bone augment material to the bone of the patient may include pressing the bone augment material into a bone void formed within the bone of the patient.

In some embodiments of the method, coupling the bone augment material to the bone of the patient may include injecting the bone augment material into a bone void formed within the bone of the patient. In these embodiments, the bone augment material may include an injectable viscous or semi-viscous fluid.

In some embodiments, the method may also include curing the bone augment material after injection to harden the bone augment material placed within the bone void.

In some embodiments of the method, forming the helical bone thread in the bone augment material may include at least one of: tapping the helical bone thread into the bone augment material with a tapping tool, and self-tapping the helical bone thread into the bone augment material with one or more self-tapping features of the bone implant.

In some embodiments of the method, the concave undercut surface of the helical thread may be angled towards one of the proximal end and the distal end of the shaft.

In some embodiments, a method of coupling a bone implant to a bone augment material may include: preparing a second interface surface of a bone augment material to receive a first interface surface of a bone implant, engaging a concave undercut surface of a helical thread of the bone implant with a convex surface of the bone augment material, and coupling at least a portion of the first interface surface of the bone implant with at least a portion of the second interface surface of the bone augment material to couple the bone implant to the bone augment material. The bone implant may include a shaft having a proximal end, a distal end, and a longitudinal axis. The bone implant may also include a helical thread disposed about the shaft along the longitudinal axis between the proximal end and the distal end of the shaft. The helical thread may include the concave undercut surface defining at least a portion of the first interface surface of the bone implant. The bone augment material may include the convex surface shaped to receive the concave undercut surface of the helical thread. The convex surface may define at least a portion of the second interface surface of the bone augment material.

In some embodiments of the method, preparing the second interface surface of the bone augment material to receive the first interface surface of the bone implant may include: coupling the bone augment material to a bone of a patient, inserting the bone implant into the bone augment material, and curing the bone augment material about the bone implant.

In some embodiments of the method, preparing the second interface surface of the bone augment material to receive the first interface surface of the bone implant may include: coupling the bone augment material to a bone of a patient, inserting a thread forming instrument into the bone augment material, curing the bone augment material about the thread forming instrument, and removing the thread forming instrument from the bone augment material.

In some embodiments of the method, preparing the second interface surface of the bone augment material to receive the first interface surface of the bone implant may include molding the bone augment material around the bone implant.

In some embodiments, the bone augment may be molded around the bone implant in situ.

In some embodiments, the bone augment may be molded around the bone implant ex situ.

In some embodiments of the method, preparing the second interface surface of the bone augment material to receive the first interface surface of the bone implant may include inserting the bone augment material through one or more openings formed in the bone implant comprising at least one of: a cannulation formed through the bone implant, and a fenestration formed in a surface of the bone implant.

In some embodiments, a bone implant system may include a bone implant and a bone augment material. The bone implant may include a shaft having a proximal end, a distal end, and a longitudinal axis. The bone implant may also include a helical thread disposed about the shaft along the longitudinal axis between the proximal end and the distal end of the shaft. The helical thread may include a concave undercut surface defining at least a portion of a first interface surface of the bone implant. The bone augment material may include a convex surface shaped to receive the concave undercut surface of the helical thread. The convex surface may define at least a portion of a second interface surface of the bone augment material. The convex surface of the bone augment material may engage the concave undercut surface of the helical thread to couple at least a portion of the first interface surface of the bone implant with at least a portion of the second interface surface of the bone augment material.

In some embodiments, the concave undercut surface of the helical thread may be angled towards one of the proximal end and the distal end of the shaft.

In some embodiments, the helical thread may include: a first undercut surface, a second undercut surface, a third undercut surface, and a fourth open surface. The first undercut surface and the third undercut surface may be angled towards one of the proximal end and the distal end of the shaft, and the second undercut surface and the fourth open surface may be angled towards the other one of the proximal end and the distal end of the shaft.

In some embodiments, the bone implant may include one or more openings configured to receive at least a portion of the bone augment material therein.

In some embodiments, at least a portion of the bone augment material may be configured to couple with a bone of a patient.

In some embodiments, the bone augment material may include a helical bone thread formed therein, the helical bone thread may include the convex surface, and the convex surface of the helical bone thread may be configured to engage the concave undercut surface of the helical thread to couple the bone implant to the bone augment material.

These and other features and advantages of the present disclosure will become more fully apparent from the following description and appended claims or may be learned by the practice of the bone implants, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure or the appended claims, the exemplary embodiments of the present disclosure will be described with additional specificity and detail through use of the accompanying drawings in which:

FIG. 1C illustrates a side view of the bone implant of FIG. 1A;

FIG. 1D illustrates a cross-sectional side view of the bone implant of FIG. 1A taken along the line A-A shown in FIG. 1C;

Figures 1A, 1B:
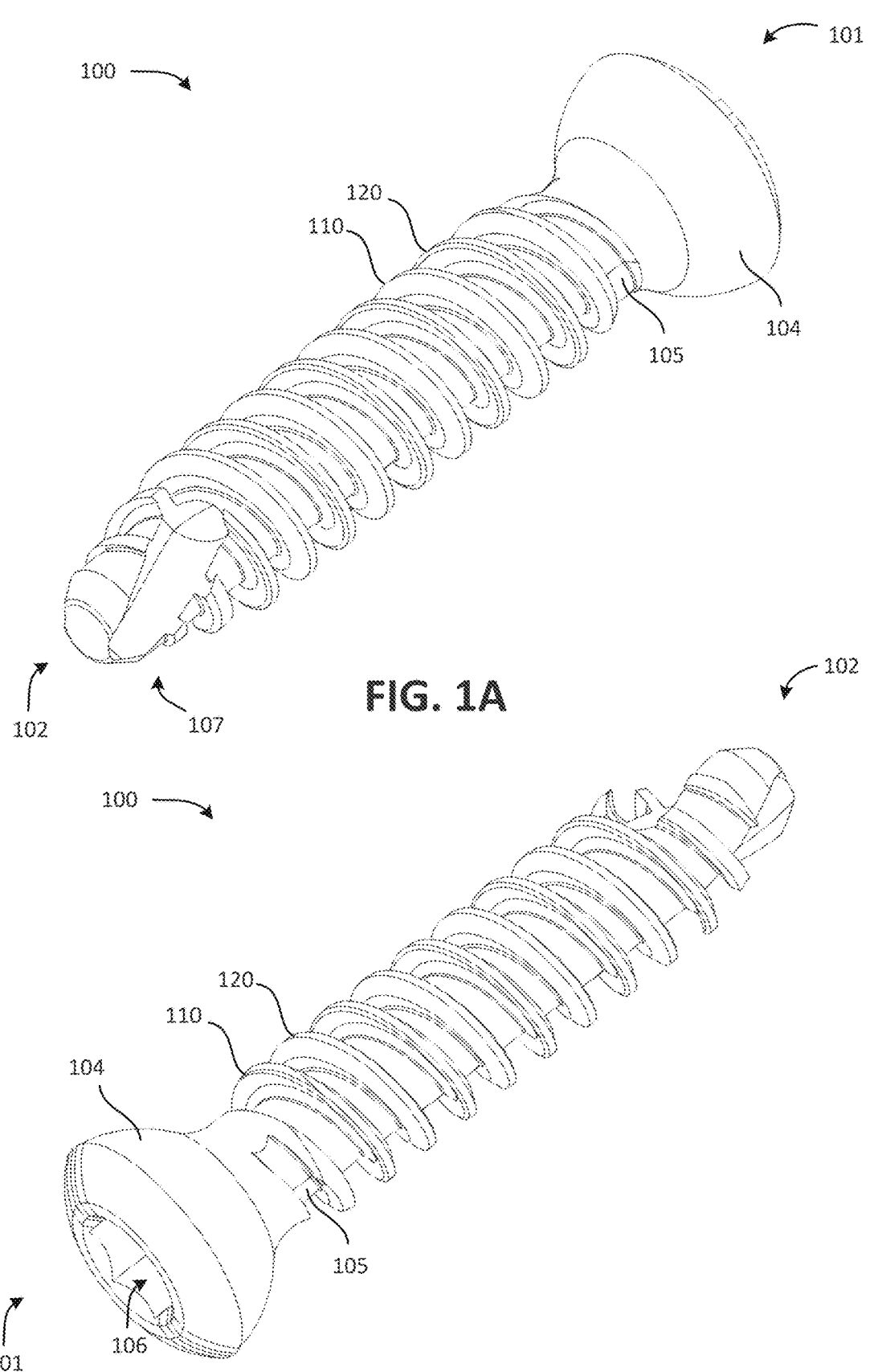
FIG. 1A illustrates a front perspective view of a fastener or bone implant, according to an embodiment of the present disclosure.
FIG. 1B illustrates a rear perspective view of the bone implant of FIG. 1A.

It is to be understood that the drawings are for purposes of illustrating the concepts of the present disclosure and may not be drawn to scale. Furthermore, the drawings illustrate exemplary embodiments and do not represent limitations to the scope of the present disclosure or the appended claims.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. *Varus* means deviation of the distal part of the leg below the knee inward, resulting in a bowlegged appearance. Valgus means deviation of the distal part of the leg below the knee outward, resulting in a knock-kneed appearance.

As used herein, the terms fastener and bone implant can comprise any device (having any structure or shape) utilizing any thread morphology described or contemplated herein that may be implanted within bone and/or bone augment material including, but not limited to: bone screws, pedicle screws, headless/headed screws, interference screws, compression screws, lag screws, long screws, half pins/Schanz fasteners, cannulated screws, threaded stems, threaded intramedullary canal bone implants, threaded joint implants (e.g., shoulder joint implants, hip joint implants, knee joint implants, etc.), bone anchors, soft tissue repair anchors, etc.

It will also be understood that any fastener or bone implant described or contemplated herein may include any thread configuration, feature, or morphology that is described or contemplated herein to achieve optimal fixation within a given bone/bone augment material. Moreover, it will also be understood that any fastener or bone implant described or contemplated herein may be utilized in conjunction with (or within) any system, method, procedure, or instrumentation that is described or contemplated herein.

FIGS. 1A-1D illustrate various views of a bone screw, bone implant, implantable bone anchor, bone disunion fastener, or fastener 100, according to an example of the present disclosure. Specifically, FIG. 1A is a front perspective view of the fastener 100, FIG. 1B is a rear perspective view of the fastener 100, FIG. 1C is a side view of the fastener 100, and FIG. 1D is a cross-sectional side view of the fastener 100 taken along the line A-A in FIG. 1C.

In general, the fastener 100 may include a shaft 105 having a proximal end 101, a distal end 102, and a longitudinal axis 103. The fastener 100 may also include a head 104 located at the proximal end 101 of the shaft 105, a torque connection interface 106 formed in/on the head 104 (in either a male/female configuration), and a self-tapping feature 107 formed in the distal end 102 of the shaft 105.

In some embodiments, the fastener 100 may include a first helical thread 110 disposed about the shaft 105, and a second helical thread 120 disposed about the shaft 105 adjacent the first helical thread 110.

In some embodiments, the fastener 100 may include a "dual start" or "dual lead" thread configuration comprising the first helical thread 110 and the second helical thread 120.

In some embodiments, a depth of the first helical thread 110 and/or the second helical thread 120 with respect to the shaft 105 may define a major diameter vs. a minor diameter of the shaft 105 alone.

In some embodiments, a major diameter and/or a minor diameter of the fastener 100 may be constant or substantially constant along the entire length of the fastener, or along a majority of the length of the fastener. In these embodiments, a constant minor diameter may help avoid blowout of narrow/delicate bones (e.g., a pedicle) when inserting a fastener into a bone. In some embodiments, a pilot hole may first be drilled into a narrow/delicate bone and then a fastener having a similar minor diameter in comparison to the diameter of the pilot hole may be chosen to avoid blowout when inserting the fastener into the bone, as will be discussed in more detail below.

In some embodiments, a depth of the first helical thread 110 and/or the second helical thread 120 with respect to the shaft 105 may vary along a length of the shaft 105 to define one or more major diameters of the fastener 100 and/or one or more regions along the fastener 100 may comprise one or more continuously variable major diameters.

In some embodiments, a thickness of the shaft 105 may vary along a length of the shaft 105 to define one or more minor diameters of the fastener 100, and/or one or more regions along the fastener 100 may comprise one or more continuously variable minor diameters.

In some embodiments, a thickness/height/width/length/pitch/angle/shape, etc., of the first helical thread 110 and/or the second helical thread 120 (or any additional helical thread) may vary along a length of the shaft 105. For example, a thickness/height/width/length/pitch/angle/shape, etc., of the first helical thread 110 and/or the second helical thread 120 may be greater towards the tip of the fastener and thinner towards the head of the fastener (or vice versa) in either a discrete or continuously variable fashion, etc.

In some embodiments, the major and/or minor diameters may increase toward a proximal end or head of a fastener in order to increase bone compaction as the fastener is terminally inserted into the bone/tissue.

In some embodiments, a pitch of the first helical thread 110 and/or the second helical thread 120 may vary along a length of the fastener 100.

In some embodiments, the fastener 100 may include a plurality of helical threads disposed about the shaft 105. However, it will also be understood that any of the fasteners disclosed or contemplated herein may include a single helical thread disposed about the shaft of the fastener. Moreover, the fastener 100 may comprise a nested plurality of helical threads having different lengths (not shown). As one non-limiting example, the fastener 100 may include a first helical thread 110 that is longer than a second helical thread 120, such that the fastener 100 comprises dual threading along a first portion of the shaft 105 and single threading along a second portion of the shaft 105.

In some embodiments, the plurality of helical threads may include three helical threads comprising a "triple start" or "triple lead" thread configuration (not shown).

In some embodiments, the plurality of helical threads may include four helical threads comprising a "quadruple start" or "quadruple lead" thread configuration (not shown).

In some embodiments, the plurality of helical threads may include more than four helical threads (not shown).

In some embodiments, the fastener 100 may include first threading with any of the shapes disclosed herein oriented toward one of the proximal end and the distal end of the fastener 100, with the first threading located proximate the distal end of the fastener 100, as well surfaces 132, and the plurality of second convex undercut surfaces 142 may comprise at least as second threading with any of the shapes disclosed herein oriented toward the other one of the proximal end and the distal end of the fastener 100, with the second threading located proximate the head of the fastener 100 (not shown).

In some embodiments, the fastener 100 may include multiple threading (e.g., dual helical threading, etc.) with any of the shapes disclosed herein located proximate one of the proximal end and the distal end of the fastener 100, as well as single threading with any of the shapes disclosed herein with the second threading located proximate the other of the proximal end and the distal end of the fastener 100.

In some embodiments, the first helical thread 110 may include a plurality of first concave undercut surfaces 131 and a plurality of first convex undercut surfaces 141.

In some embodiments, the second helical thread 120 may include a plurality of second concave undercut surfaces 132 and a plurality of second convex undercut surfaces 142.

In some embodiments, when the fastener 100 is viewed in section along a plane that intersects the longitudinal axis 103 of the shaft 105 (e.g., see FIG. 1D), the plurality of first concave undercut surfaces 131 and the plurality of second convex undercut surfaces 142 may be oriented toward (i.e., point toward) the proximal end 101 of the shaft 105.

In some embodiments, the plurality of first convex undercut surfaces 141 and the plurality of second concave undercut surfaces 132 may be oriented toward (i.e., point toward) the distal end 102 of the shaft 105.

In some embodiments, at least one of the plurality of first concave undercut surfaces 131, the plurality of first convex undercut surfaces 141, the plurality of second concave undercut one substantially flat surface.

In some embodiments, when the fastener 100 is viewed in section along a plane intersecting the longitudinal axis 103 of the shaft 105, the first helical thread 110 may comprise a plurality of first bent shapes (comprising at least one surface that is angled relative to the longitudinal axis 103 of the shaft 105 and/or at least one undercut surface) with a plurality of first intermediate portions 151 that are oriented toward (i.e., point toward) the distal end 102 of the shaft 105. This may be referred to as "standard" threading, having a "standard" orientation.

In some embodiments, when the fastener 100 is viewed in section along a plane intersecting the longitudinal axis 103 of the shaft 105, the second helical thread 120 may comprise a plurality of second bent shapes (comprising at least one surface that is angled relative to the longitudinal axis 103 of the shaft 105 and/or at least one undercut surface) with a plurality of second intermediate portions 152 that are oriented toward (i.e., point toward) the proximal end 101 of the shaft 105. This may be referred to as "inverted" threading, having an "inverted" orientation.

In some embodiments, one or more helical threads may morph/transition between a standard orientation and an inverted orientation along a shaft of a fastener.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one curved surface.

As shown in FIG. 1D, the proximally-oriented and distally-oriented surfaces of the first helical thread 110 (i.e., the first concave undercut surfaces 131 and the first convex undercut surfaces 141 in the fastener 100 of FIG. 1D) may not have mirror symmetry relative to each other about any plane perpendicular to the longitudinal axis 103 of the fastener 100. Rather, the first concave undercut surfaces 131 and the first convex undercut surfaces 141 may be generally second concave undercut surfaces 132 and the second convex undercut surfaces 142 may not have mirror symmetry relative to each other but may be generally parallel to each other.

Conversely, as also shown in FIG. 1D, the proximally-oriented surfaces of the first helical thread 110 may have mirror symmetry relative to the distally-oriented surfaces of the parallel to each other. The same may be true for the second helical thread 120, in which the second helical thread 120. Specifically, the first concave undercut surfaces 131 may have mirror symmetry relative to the second convex undercut surfaces 142 about a plane 170 that bisects the space between them and lies perpendicular to the longitudinal axis 103.

Similarly, the distally-oriented surfaces of the first helical thread 110 may have mirror symmetry relative to the proximally-oriented surfaces of the second helical thread 120. Specifically, the second concave undercut surfaces 132 may have mirror symmetry relative to the first convex undercut surfaces 141 about a plane 172 that bisects the space between them and lies perpendicular to the longitudinal axis 103.

This mirror symmetry may be present along most of the length of the first helical thread 110 and the second helical thread 120, with symmetry across different planes arranged between adjacent turns of the first helical thread 110 and the second helical thread 120 along the length of the longitudinal axis 103. Such mirror symmetry may help more effectively capture bone between the first helical thread 110 and the second helical thread 120 and may also facilitate manufacture of the fastener 100.

Figure 2:
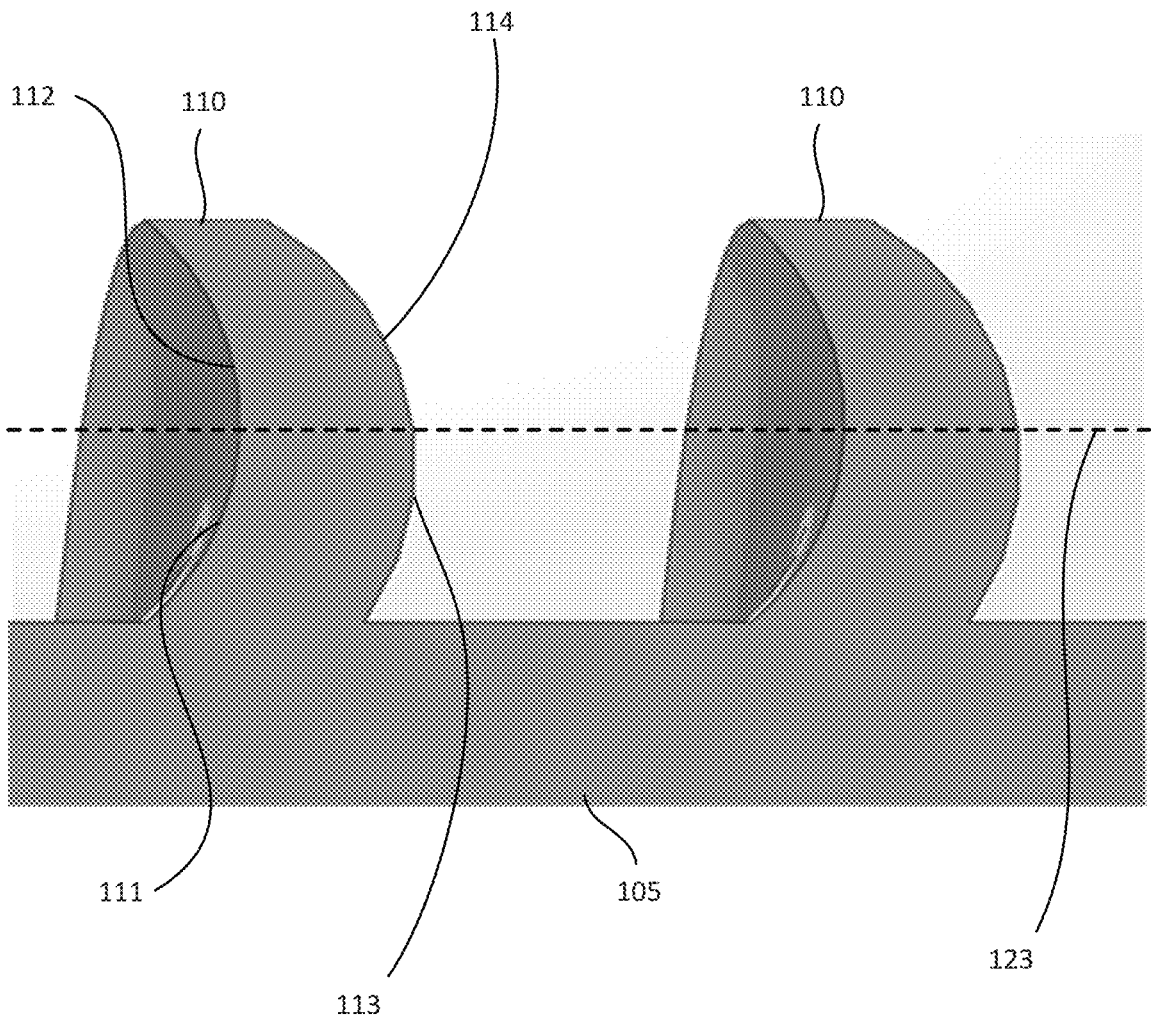
FIG. 2 illustrates a partial cross-sectional side view of a bone implant comprising crescent-shaped threading.

In some embodiments, when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105 and/or the proximal end 101 of the shaft 105. FIG. 2 illustrates a partial cross-sectional view of a fastener comprising crescent shapes, as one non-limiting example of such an embodiment.

In some embodiments (not shown), when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105, and the second helical thread 120 may include at least one partial crescent shape that is oriented toward (i.e., points toward) the proximal end 101 of the shaft 105.

In some embodiments (not shown), the first helical thread 110 may include a first plurality of partial crescent shapes that are oriented toward (i.e., point toward) the distal end 102 of the shaft 105, and the second helical thread 120 may include a second plurality of partial crescent shapes that are oriented toward (i.e., point toward) the proximal end 101 of the shaft 105.

In some embodiments (not shown), the first plurality of partial crescent shapes and the second plurality of partial crescent shapes may be arranged in alternating succession along the shaft 105 of the fastener 100.

In some embodiments, the first helical thread 110 may be bisected by the line 123 shown in FIG. 2 with each crescent shape including a plurality of first undercut surfaces 111, a plurality of second undercut surfaces 112, a plurality of third undercut surfaces 113, and a plurality of fourth open surfaces 114 similar to the helical threading shown in FIG. 1D, except with curved surfaces in place of flat surfaces.

In some embodiments, the plurality of first undercut surfaces 111 and the plurality of second undercut surfaces 112 may comprise concave curved surfaces. However, it will be understood that portions of the plurality of first undercut surfaces 111 and/or portions of the plurality of second undercut surfaces 112 may also comprise convex curved surfaces and/or flat surfaces (not shown in FIG. 2).

In some embodiments, the plurality of third undercut surfaces 113 and the plurality of fourth open surfaces 114 may comprise convex curved surfaces. However, it will be understood that portions of the plurality of third undercut surfaces 113 and the plurality of fourth open surfaces 114 may also comprise concave curved surfaces and/or flat surfaces (not shown in FIG. 2).

In some embodiments, the plurality of third undercut surfaces 113 and the plurality of fourth open surfaces 114 may be replaced by a ramped surface (such as that utilized in a standard buttress thread design) without any undercuts (not shown in FIG. 2). Likewise, any of the other thread designs disclosed herein may utilize a ramped or buttress thread design on at least one side of the helical thread.

In some embodiments, a fastener may have only standard threads or only inverted threads. The type of threads that are desired may depend on the type and/or magnitude of loads to be applied to the fastener. For example, a screw loaded axially away from the bone in which it is implanted may advantageously have a standard thread, while a screw loaded axially toward the bone in which it is implanted may advantageously have an inverted thread. A screw that may experience multi-axial loading and/or off-loading conditions may advantageously include at least one standard thread and at least one inverted thread in order to increase bone fixation and load sharing between a bone/fastener interface during multi-axial and off-loading conditions to reduce high bone strain and distribute multi-axial forces applied to the bone in a load-sharing, rather than load-bearing, configuration. Shear loads and/or bending moments may also be optimally resisted with any chosen combination of threading, threading morphology, and/or threading variations contemplated herein to optimally resist shear loads, bending moments, multi-axial loading, off-loading conditions, etc.

In some embodiments, fasteners with standard threads may be used in conjunction with fasteners with inverted threads in order to accommodate different loading patterns.

In some embodiments, a single fastener may have both standard and inverted threads, like the fastener 100. Such a combination of threads may help the fastener 100 remain in place with unknown and/or varying loading patterns.

In some embodiments, the geometry of the threading of a fastener (with standard and/or inverted threads) may be varied to suit the fastener for a particular loading scheme. For example, the number of threads, the number of thread starts, the pitch of the threading, the lead(s) of the threading, the shape(s) of the threading, any dimension(s) associated with the threading (e.g., any length(s)/width(s)/height(s)/ inflection point(s), etc., associated with the threading), the major diameter(s), the minor diameter(s), any angulation/ angles associated with any surfaces of the threading, the "handedness" of the threading (e.g., right-handed vs. left-handed), etc., may be varied accordingly to suit any specific medium of installation, loading pattern, desired radial loading force, pull-out strength, application, procedure, etc., that may be involved.

In some embodiments, the material(s) of any portion of a bone implant, joint replacement implant, fastener, bone disunion fastener, etc., described herein may include, but are not limited to: metals (e.g., titanium, cobalt, stainless steel, etc.), metal alloys, plastics, polymers, ceramics, PEEK, UHMWPE, composites, additive particles, textured surfaces, biologics, biomaterials, bone, etc.

In some embodiments, any of the fasteners or bone implants described herein may include additional features such as: self-tapping features, locking features (e.g., locking threading formed on a portion of the fastener, such as threading located on or near a head of the fastener), opening(s), cannulation(s), fenestration(s), any style of fastener head (or no fastener head at all), any style of torque connection interface (or no torque connection interface at all), etc.

In some embodiments, any of the fasteners or bone implants described herein may also include opening(s), cannulation(s), fenestration(s), etc., that may be configured to receive any suitable bone cement or bone augment material therein to facilitate bone in-growth, bone fusion, etc.

In some embodiments, a tap (not shown) may be utilized to pre-form threading in a bone or bone augment material according to any threading shape that is disclosed or contemplated herein. In this manner, taps with any suitable shape may be utilized in conjunction with any fastener described or contemplated herein to match or substantially match the threading geometry of a given fastener or bone implant.

In some embodiments, a minor diameter of the fastener may be selected to match, or substantially match, a diameter of a pilot hole that is formed in a bone to avoid bone blowout when the fastener is inserted into the pilot hole.

Additionally, or alternatively thereto, the type of threads and/or thread geometry may be varied based on the type of bone in which the fastener is to be anchored. For example, fasteners anchored in osteoporotic bone may fare better with standard or inverted threads, or when the pitch, major diameter, and/or minor diameter are increased or decreased, or when the angulation of thread surfaces is adjusted, etc.

In some embodiments, a surgical kit may include one or more bone implants with any of the different thread options described or contemplated herein. The surgical kit may also include any of the instruments described herein. The surgical kit may also include any bone augment materials that are described or contemplated herein. The surgeon may select the appropriate bone implants from the kit based on the particular loads to be applied and/or the quality of bone in which the bone implants are to be anchored.

Continuing with FIG. 1D, in some embodiments the first helical thread 110 may include a plurality of first undercut surfaces 111, a plurality of second undercut surfaces 112, a plurality of third undercut surfaces 113, and a plurality of fourth open surfaces 114.

In some embodiments, the second helical thread 120 may include a plurality of fifth undercut surfaces 125, a plurality of sixth undercut surfaces 126, a plurality of seventh undercut surfaces 127, and a plurality of eighth open surfaces 128.

In some embodiments, one or more of the plurality of first undercut surfaces 111, the plurality of second undercut surfaces 112, the plurality of third undercut surfaces 113, the plurality of fourth open surfaces 114, the plurality of fifth undercut surfaces 125, the plurality of sixth undercut surfaces 126, the plurality of seventh undercut surfaces 127, and the plurality of eighth open surfaces 128 may comprise at least one flat or substantially flat surface.

In some embodiments, the plurality of first undercut surfaces 111, the plurality of third undercut surfaces 113, the plurality of sixth undercut surfaces 126, and the plurality of eighth open surfaces 128 may be angled towards the distal end 102 of the shaft 105.

In some embodiments, the plurality of second undercut surfaces 112, the plurality of fourth open surfaces 114, the plurality of fifth undercut surfaces 125, and the plurality of seventh undercut surfaces 127 may be angled towards the proximal end 101 of the shaft 105.

In some embodiments, when the fastener 100 is viewed in section along a plane that intersects the longitudinal axis 103 of the shaft 105 (as shown in FIG. 1D), the first helical thread 110 may include at least one chevron shape that is oriented toward (i.e., points toward) the distal end 102 of the shaft 105. Likewise, the second helical thread 120 may also include at least one chevron shape that is oriented toward (i.e., points toward) the proximal end 101 of the shaft 105.

In some embodiments, when the fastener 100 is viewed in section along a plane that intersects the longitudinal axis 103 of the shaft 105 (as shown in FIG. 1D), the first helical thread 110 may include a first plurality of chevron shapes that are oriented toward (i.e., point toward) the distal end 102 of the shaft 105. Likewise, the second helical thread 120 may include a second plurality of chevron shapes that are oriented toward (i.e., point toward) the proximal end 101 of the shaft 105.

In some embodiments, the first plurality of chevron shapes and the second plurality of chevron shapes may be arranged in alternating succession along the shaft 105 of the fastener 100, (e.g., see FIG. 1D).

In some embodiments, a plurality of first interlocking spaces 161 and a plurality of second interlocking spaces 162 may be formed between the first helical thread 110 and the second helical thread 120 along the shaft 105 of the fastener 100.

In some embodiments, the plurality of first interlocking spaces 161 may be formed intermediate the first concave undercut surfaces 131 and the second concave undercut surfaces 132.

In some embodiments, the plurality of second interlocking spaces 162 may be formed intermediate the first convex undercut surfaces 141 and the second convex undercut surfaces 142.

In some embodiments, the plurality of first interlocking spaces 161 may be larger in size than the plurality of second interlocking spaces.

In some embodiments, the plurality of first interlocking spaces 161 and the plurality of second interlocking spaces 162 may be shaped and/or configured to interlock with bone/other tissues received therein to increase fixation of the fastener 100 within the bone/other tissues and provide additional resistance against multi-axial forces that may be applied to the fastener 100 and/or the bone/other tissues.

In some embodiments, the plurality of second undercut surfaces 112 and the plurality of sixth undercut surfaces 126 may be angled toward each other to trap bone/bone augment material within the plurality of first interlocking spaces 161 in order to increase fixation and resistance against multi-axial forces.

In some embodiments, the plurality of third undercut surfaces 113 and the plurality of seventh undercut surfaces 127 may be angled toward each other to trap bone/other tissues within the plurality of second interlocking spaces 162 in order to increase fixation and resistance against multi-axial forces.

In some embodiments, the plurality of first undercut surfaces 111 and the plurality of fifth undercut surfaces 125 may each form an angle $\alpha$ with respect to the longitudinal axis 103 of the shaft 105, as shown in FIG. 1D.

In some embodiments, the angle $\alpha$ may be greater than 90 degrees.

In some embodiments, the plurality of second undercut surfaces 112 and the plurality of sixth undercut surfaces 126 may each form an angle $\beta$ with respect to the longitudinal axis 103 of the shaft 105.

In some embodiments, the angle $\beta$ may be less than 90 degrees.

In some embodiments, the plurality of third undercut surfaces 113 and the plurality of seventh undercut surfaces 127 may each form an angle $\theta$ with respect to the longitudinal axis 103 of the shaft 105.

In some embodiments, the angle $\theta$ may be approximately 90 degrees.

In some embodiments, the angle $\theta$ may be greater than 90 degrees.

It will be understood that any fastener or bone implant described or contemplated herein may include any thread configuration, feature, or morphology that is described or contemplated herein to achieve optimal fixation within a given bone/tissue. Moreover, it will also be understood that any fastener or bone implant that is described or contemplated herein may be utilized in conjunction with (or within) any system, method, or instrumentation that is described or contemplated herein.

Figure 3:
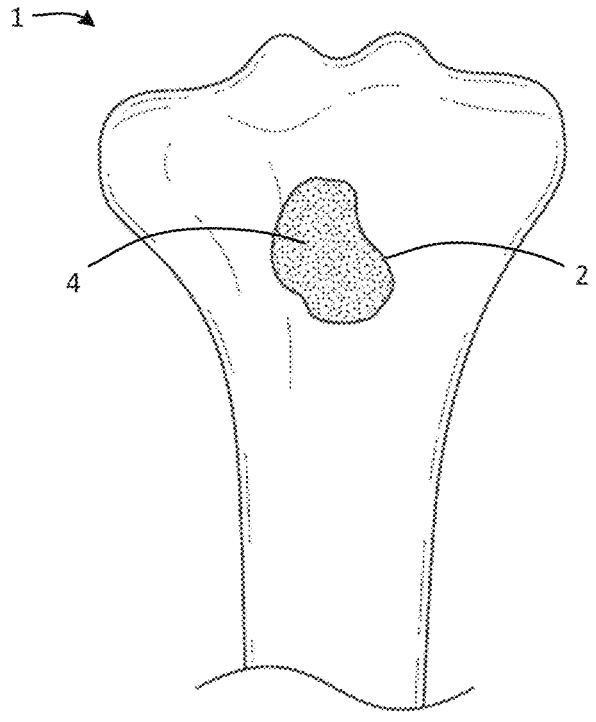
FIG. 3 illustrates a bone with a void that is filled with bone augment material, according to an embodiment of the present disclosure.

FIG. 3 illustrates a bone 1 having a bone void 2 filled with a bone void filler or bone augment material 4, according to an example of the present disclosure.

The bone 1 may represent any bone of a patient including, but not limited to: a fibula, an ulna, a humerus, a tibia, a femur, a shoulder bone, a finger bone, a toe bone, etc.

The bone augment material 4 may comprise any material, media, or substance that may help strengthen or support a bone defect (e.g., a bone void 2, a bone fracture 3, osteoporotic bone, weak/soft bone, etc.). The bone augment material 4 may include, but is not limited to: native or natural bone materials, non-native, artificial, or synthetic bone materials, bone cement, hydroxyapatite, biomaterials, biologics, bone morphogenetic proteins, PEEK, composites, additive particles, plastics, polymers, ceramics, UHMWPE, metals (e.g., titanium, cobalt, stainless steel, etc.), metal alloys, etc.

In some embodiments, the bone augment material 4 may comprise a liquid or viscous material (e.g., such as a viscous bone cement material before it has cured or hardened).

In some embodiments, the bone augment material 4 may comprise a semi-liquid, semi-viscous, or semi-solid material (e.g., such as a putty-like material or paste that may be molded or shaped by hand).

In some embodiments, the bone augment material 4 may comprise a rigid or solid material that may be shaped by drilling, tapping, reaming, broaching, etc.

In some embodiments, the bone augment material 4 may comprise a liquid/viscous material (or a semi-liquid/viscous/ solid material) that may be capable of hardening, setting-up, or curing into a rigid or solid material.

Figure 4:
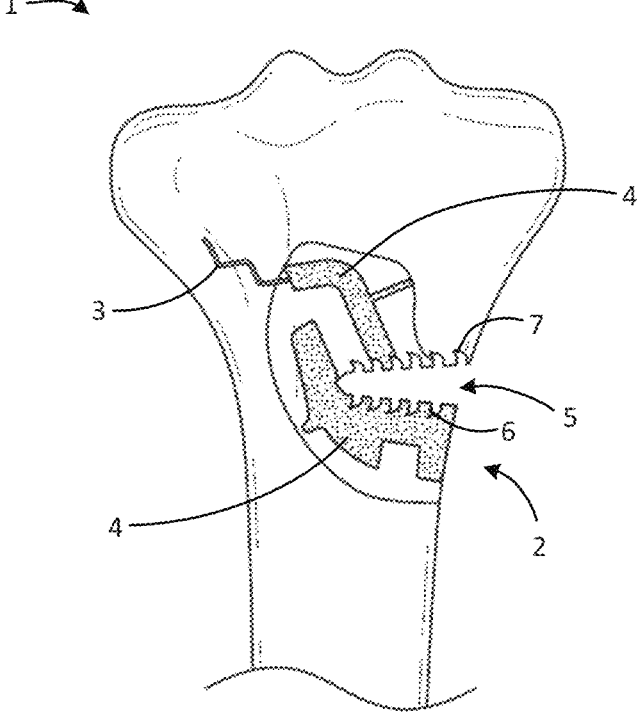
FIG. 4 illustrates a bone comprising a bone augment material with a helical bone thread formed therein, according to an embodiment of the present disclosure.

FIG. 4 illustrates a bone 1 comprising a bone augment material 4 with a helical bone thread 7 formed therein, according to another example of the present disclosure. The bone augment material 4 may help stabilize and strengthen the bone void 2 and/or the bone fracture 3 shown in FIG. 4.

In some embodiments, at least a portion of the bone augment material 4 may be coupled to the bone 1, as shown in FIG. 4, or may be coupled to/within any bone of a patient.

Figure 5:
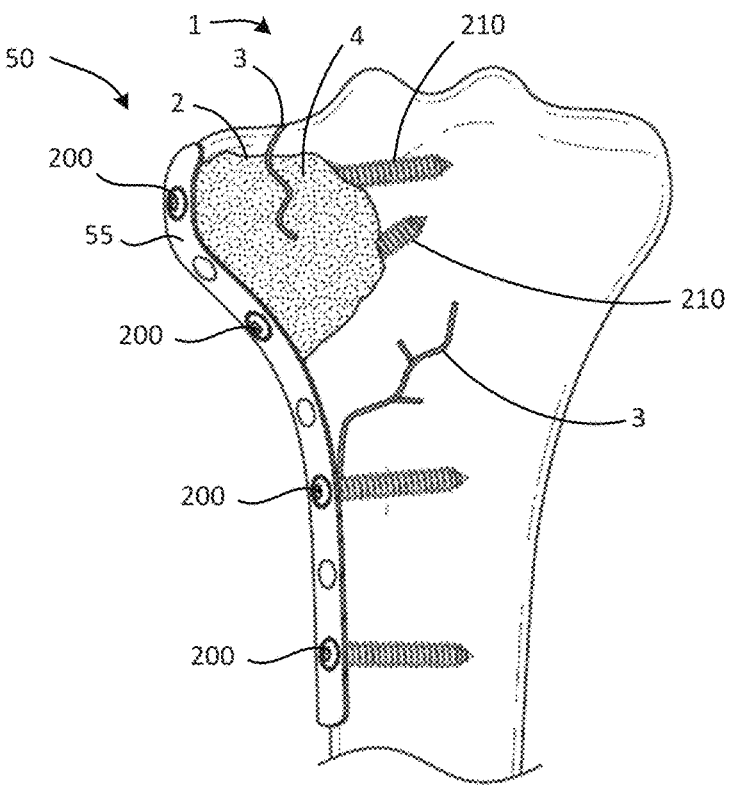
FIG. 5 illustrates a bone comprising a bone implant system, according to an embodiment of the present disclosure.
Figure 6:
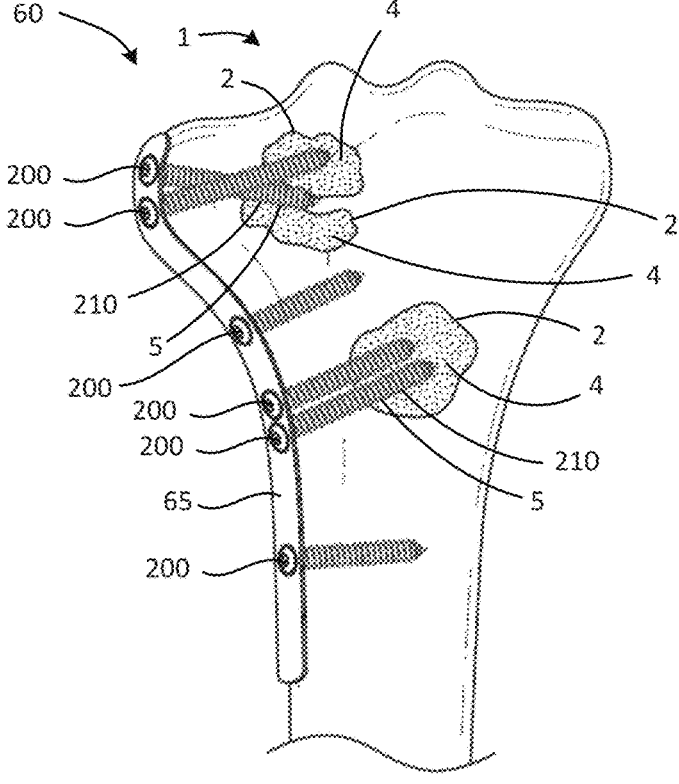
FIG. 6 illustrates a bone comprising a bone implant system, according to another embodiment of the present disclosure.

In some embodiments, the helical bone thread 7 formed in the bone augment material 4 may at least partially define a second interface surface 5 of the bone augment material 4 that may be configured to couple with a first interface surface 210 of a bone implant 200, as shown in FIGS. 5 and 6 as just two non-limiting examples. Specifically, FIG. 5 illustrates a bone 1 comprising a bone implant system 50 that may include bone augment material 4, one or more bone implants 200, and a fracture repair or bone plate 55, and FIG. 6 illustrates a bone 1 comprising a bone implant system 60 that may include bone augment material 4, one or more bone implants 200, and a bone plate 65.

Figure 7A:
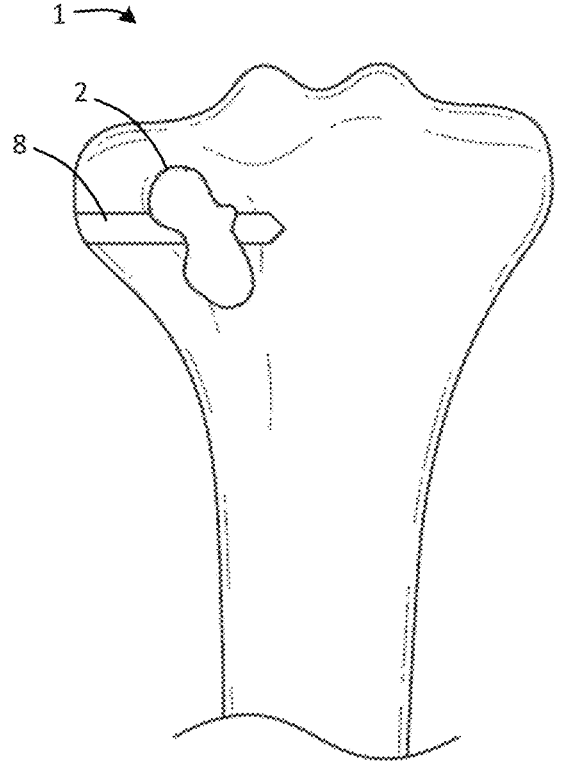
FIGS. 7A-7D illustrate methods for preparing a bone with a bone augment material to couple with a bone implant, according to embodiments of the present disclosure.
Figure 7B:
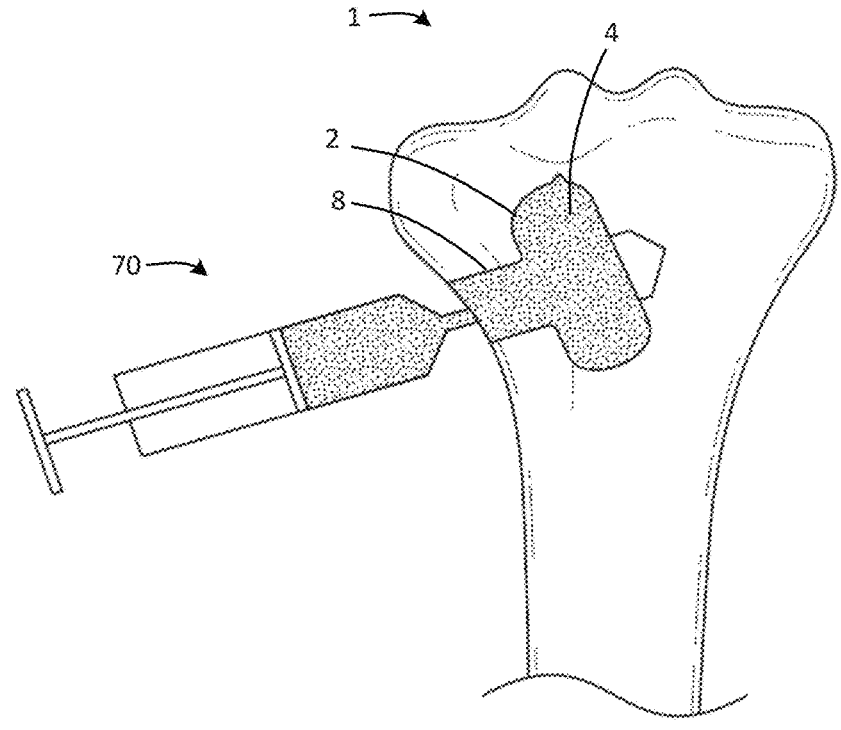
Figure 7C:
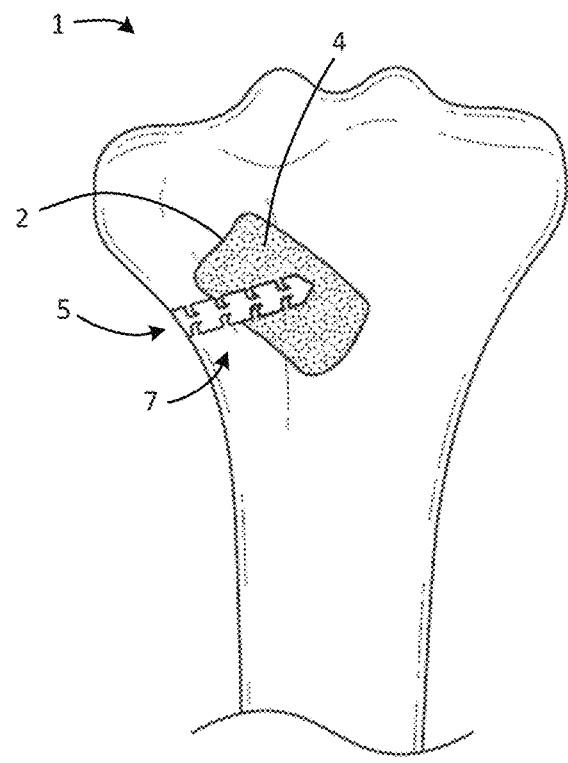
Figure 7D:
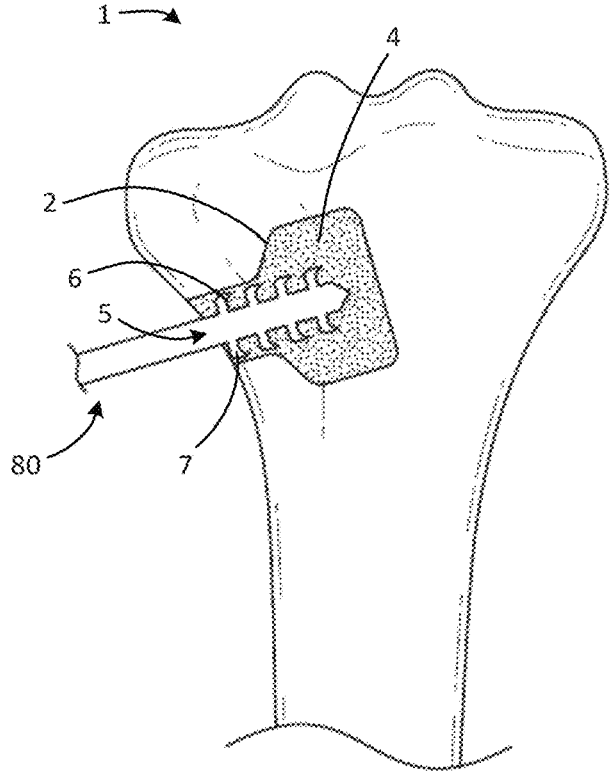

In some embodiments, the helical bone thread 7 formed in the bone augment material 4 may comprise a convex surface 6, as shown in FIGS. 4 and 7D.

In some embodiments, the convex surface 6 of the helical bone thread 7 may at least partially define the second interface surface 5 of the bone augment material 4.

In some embodiments, the convex surface 6 may be shaped to receive a concave undercut surface of a helical thread that is disposed about the bone implant 200, as previously described with respect to FIGS. 1A-2. It will be understood that the convex surface 6 may include any size/shape suitable to receive any size/shape concave undercut surface of any helical thread disposed about the bone implant 200 described or contemplated herein. Moreover, it will also be understood that the bone implant 200 may comprise any type of bone implant with any helical thread shape or morphology described or contemplated herein including, but not limited to: bone screws, pedicle screws, headless/headed screws, interference screws, compression screws, lag screws, long screws, half pins/Schanz fasteners, cannulated screws, threaded stems, threaded intramedullary canal bone implants, threaded joint implants (e.g., shoulder joint implants, hip joint implants, knee joint implants, etc.), bone anchors, soft tissue repair anchors, etc.

In some embodiments, the concave undercut surface of the helical thread disposed about the bone implant 200 may be angled towards one of the proximal end and the distal end of the shaft of the bone implant 200. However, it will also be understood that the bone implant 200 may include any thread configuration, feature, or morphology described or contemplated herein with respect to any fastener/bone implant to achieve optimal fixation within a given bone/bone augment material. For example, in some embodiments the helical thread may comprise standard or inverted threading, a "dual start" thread configuration, etc. Moreover, it will also be understood that the bone implant 200 may be utilized in conjunction with (or within) any system, method, procedure, or instrumentation that is described or contemplated herein.

In some embodiments, the helical bone thread 7 comprising the convex surface 6 formed in the bone augment material 4 may be configured to receive a helical thread of the bone implant 200 therein. The convex surface 6 formed in the bone augment material 4 may be configured to engage the concave undercut surface of the helical thread disposed about the bone implant 200 to couple at least a portion of the first interface surface 210 of the bone implant 200 with at least a portion of the second interface surface 5 of the bone augment material 4. In this manner, the bone implant 200 may securely couple with the bone augment material 4.

In some embodiments, a bone implant system may include a bone implant 200 and a bone augment material 4. The bone implant 200 may include a shaft 105 having a proximal end 101, a distal end 102, and a longitudinal axis 103. The bone implant 200 may also include at least one helical thread disposed about the shaft 105 along the longitudinal axis 103 between the proximal end 101 and the distal end 102 of the shaft 105. The helical thread may include a concave undercut surface defining at least a portion of a first interface surface 210 of the bone implant 200. The bone augment material 4 may include a convex surface 6 shaped to receive the concave undercut surface of the helical thread. The convex surface 6 may define at least a portion of a second interface surface 5 of the bone augment material 4. The convex surface 6 of the bone augment material 4 may engage the concave undercut surface of the helical thread to couple at least a portion of the first interface surface 210 of the bone implant 200 with at least a portion of the second interface surface 5 of the bone augment material 4.

In some embodiments, the concave undercut surface of the helical thread may be angled towards one of the proximal end 101 and the distal end 102 of the shaft 105.

In some embodiments, the helical thread may include: a first undercut surface 111, a second undercut surface 112, a third undercut surface 113, and a fourth open surface 114. The first undercut surface 111 and the third undercut surface 113 may be angled towards one of the proximal end 101 and the distal end 102 of the shaft 105, and the second undercut surface 112 and the fourth open surface 114 may be angled towards the other one of the proximal end 101 and the distal end 102 of the shaft 105.

In some embodiments, the bone implant 200 may comprise one or more openings (not shown) formed in the bone implant 200 that may be configured to receive the bone augment material 4 therethrough in order to help form the second interface surface 5 of the bone augment material 4 about the first interface surface 210 of the bone implant 200.

In some embodiments, the bone implant 200 may comprise one or more cannulations (not shown) that may be configured to receive the bone augment material 4 therethrough to help form the second interface surface 5 of the bone augment material 4 about the first interface surface 210 of the bone implant 200.

In some embodiments, the bone implant 200 may comprise one or more fenestrations (not shown) in fluid communication with the one or more cannulations and/or the one or more openings. The one or more fenestrations may be configured to receive the bone augment material 4 therethrough to help form the second interface surface 5 of the bone augment material 4 about the first interface surface 210 of the bone implant 200.

FIGS. 7A-7D illustrate a method, surgical procedure, or procedure for preparing a bone augment material 4 to couple with a bone implant 200, according to examples of the present disclosure.

In some embodiments of the procedure, a bone defect (such as a bone void 2, a bone fracture 3, weak bone, etc.) may be detected in the bone 1, either during the surgical procedure or before the surgical procedure via one or more imaging techniques.

In some embodiments of the procedure, a bone tunnel 8 may be drilled in the bone 1 with a suitable drill tool (not shown) to provide access to the bone defect, as shown in FIG. 7A.

In some embodiments of the procedure, bone augment material 4 may be coupled to the bone 1. For example, in some embodiments a bone augment material inserter 70 or injector may be utilized to insert a viscous or semi-viscous bone augment material 4 through the bone tunnel 8 and into the bone void 2, as shown in FIG. 7B. In some embodiments, the viscous or semi-viscous bone augment material 4 may then be allowed to cure, set, or harden within the bone defect. In other embodiments, the bone augment material may be pressed into a bone void (e.g., for less liquid/viscous bone augment materials).

In some embodiments of the procedure, the hardened bone augment material 4 may then be drilled, tapped, reamed, broached, etc., to form a helical bone thread 7 having a desired shape within the bone augment material 4, as shown in FIG. 7C. In some embodiments, the helical bone thread 7 may comprise the convex surface 6 and may at least partially define the second interface surface 5 of the bone augment material 4 configured to couple with the first interface surface 210 of the bone implant 200, as previously described.

In some embodiments of the procedure, the helical bone thread 7 may be tapped into the hardened bone augment material 4 with a tapping tool (not shown) that may comprise helical threading of any shape or morphology necessary to produce a complementary shape for any of the helical thread designs, shapes, or morphologies that are described or contemplated herein.

In some embodiments of the procedure, the helical bone thread 7 may be formed (or at least partially formed) in the hardened bone augment material 4 by inserting a bone implant comprising self-tapping features into the bone augment material 4. In these embodiments, a tapping tool may or may not be utilized.

Alternatively, in some embodiments of the procedure the helical bone thread 7 may be formed in the bone augment material 4 by placing a thread forming instrument 80 within the viscous or semi-viscous bone augment material 4 before it has cured, set, or hardened within the bone defect, as shown in FIG. 7D. The thread forming instrument 80 may include any instrument comprising helical threading with any shape necessary to produce a complementary shape for any of the helical thread designs, shapes, or morphologies described or contemplated herein. For example, the thread forming instrument 80 may include, but is not limited to: a standalone instrument, such as a mold, a tap, etc., or a portion of another instrument, such as a portion of the bone augment material inserter 70 or injector, etc.

In some embodiments, a method of coupling the bone implant 200 to the bone augment material 4 may include preparing the second interface surface 5 of the bone augment material 4 to receive the first interface surface 210 of the bone implant 200, engaging the concave undercut surface of the helical thread disposed about the bone implant 200 with the convex surface 6 of the bone augment material 4, and coupling at least a portion of the first interface surface 210 of the bone implant 200 with at least a portion of the second interface surface 5 of the bone augment material 4 in order to couple the bone implant 200 to the bone augment material 4.

In some embodiments, the method may also include coupling at least a portion of the bone augment material 4 to a bone 1 of a patient.

In some embodiments of the method, preparing the second interface surface 5 of the bone augment material 4 to receive the first interface surface 210 of the bone implant 200 may include: coupling the bone augment material 4 to the bone 1 of a patient, curing/hardening the bone augment material 4, and forming the helical bone thread 7 in the bone augment material 4.

In some embodiments of the method, forming the helical bone thread 7 in the bone augment material 4 may include at least one of: tapping the helical bone thread 7 into the bone augment material 4 with a tapping tool (not shown), and self-tapping the helical bone thread 7 into the bone augment material 4 with one or more self-tapping features of the bone implant 200.

In some embodiments of the method, preparing the second interface surface 5 of the bone augment material 4 to receive the first interface surface 210 of the bone implant 200 may include: coupling the bone augment material 4 to a bone 1 of a patient, inserting the bone implant 200 into the bone augment material 4, and curing the bone augment material 4 about the bone implant 200.

In some embodiments of the method, preparing the second interface surface 5 of the bone augment material 4 to receive the first interface surface 210 of the bone implant 200 may include: coupling the bone augment material 4 to a bone 1 of a patient, inserting a thread forming instrument 80 into the bone augment material 4, curing/hardening the bone augment material 4 about the thread forming instrument 80, and removing the thread forming instrument 80 from the cured/hardened bone augment material 4.

In some embodiments of the method, preparing the second interface surface 5 of the bone augment material 4 to receive the first interface surface 210 of the bone implant 200 may include molding the bone augment material 4 around the bone implant 200 or thread forming instrument 80.

In some embodiments of the method, the bone augment material 4 may be molded or formed around the bone implant 200 or thread forming instrument 80 in situ (e.g., within the bone/bone defect area).

In some embodiments of the method, the bone augment material 4 may be molded or formed around the bone implant 200 or thread forming instrument 80 ex situ (e.g., outside of the bone/bone defect area). In these embodiments, the molded/formed bone augment material 4 and/or the bone implant 200 may then be placed into the bone/bone defect area, either separately, or together.

In some embodiments of the method, the bone augment material 4 may be inserted through one or more openings (not shown) formed in the bone implant 200.

In some embodiments of the method, the bone augment material 4 may be inserted through one or more cannulations (not shown) formed through at least a portion of the bone implant 200.

In some embodiments of the method, the bone augment material 4 may be inserted through the one or more cannulations and out of one or more fenestrations (not shown) formed in the bone implant 200 that may be in fluid communication with the one or more cannulations.

Any procedures or methods disclosed herein comprise one or more steps or actions for performing the described procedure or method. The method steps and/or actions may be interchanged with one another. In other words, unless a specific order of steps or actions is required for proper operation of the embodiment, the order and/or use of specific steps and/or actions may be modified. Moreover, any of the methods or procedures described herein may be further modified by omitting, deleting, and/or adding any of the method, procedure steps, or actions described or contemplated herein.

Any of the bone implants described or contemplated herein may be configured for removal and replacement during a revision procedure by simply unscrewing and removing the bone implant from the bone/bone augment material in which the bone implant resides. Moreover, the bone implants described herein may advantageously be removed from bone and/or the bone augment material 4 without removing any appreciable amount of the bone or bone augment material 4 during the removal process in order to preserve the bone and/or bone augment material 4. In this manner, bone implants may be mechanically integrated with the bone/bone augment material, while not being permanently affixed to the bone/bone augment material or integrated via bony ingrowth, in order to provide an instant and removable connection between the bone implant and the bone/bone augment material. Accordingly, revision procedures utilizing the bone implants described herein can result in less trauma to the bone/bone augment material with improved patient outcomes. However, it will also be understood that any of the bone implants described or contemplated herein may also be permanently or semi-permanently affixed to a bone/bone augment material via a strong bond with the bone/bone augment material (e.g., via bony ingrowth, etc.), as desired.

It will be understood than any feature or group of features described or contemplated herein with respect to any implant, system, method, or instrument may be combined in any fashion with any other implant, system, method, or instrument that is described or contemplated herein in order to make any number of different implant, system, method, or instrument configurations.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

The phrases "connected to", "coupled to", and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the devices, instruments, systems, and methods disclosed herein.

What is claimed is:

1. A method of coupling a bone implant to a bone augment material comprising:

Coupling the bone augment material to a bone of a patient such that all of the bone augment material couples to the bone of the patient as a viscous fluid passed through a single aperture of a bone augment material inserter to couple with the bone of the patient;

after the bone augment material has been coupled to the bone of the patient, inserting a thread-forming tool into the bone augment material and forming a helical bone thread in the bone augment material, wherein the thread-forming tool is separate from the bone implant; and coupling the bone implant to the helical bone thread formed in the bone augment material, wherein:

the bone implant comprises:

a shaft comprising:
a proximal end;
a distal end; and
a longitudinal axis; and a helical thread disposed about the shaft along the longitudinal axis between the proximal end and the distal end of the shaft, wherein the helical thread comprises a concave undercut surface, wherein the helical bone thread formed in the bone augment material comprises a convex surface shaped to engage the concave undercut surface of the bone implant to couple the bone implant to the bone augment material.

2. The method of claim 1, wherein the bone augment material comprises at least one of:

a bone cement;
a natural bone graft material; and
an artificial bone graft material.

3. The method of claim 1, wherein coupling the bone augment material to the bone of the patient further comprises:

injecting the bone augment material into a bone void formed within the bone of the patient, wherein the bone augment material comprises an injectable viscous fluid.

4. The method of claim 3, further comprising:

curing the bone augment material after injection to harden the bone augment material placed within the bone void.

5. The method of claim 1, wherein forming the helical bone thread in the bone augment material further comprises tapping the helical bone thread into the bone augment material with a tapping tool.

6. The method of claim 1, wherein the concave undercut surface of the helical thread is angled towards one of the proximal end and the distal end of the shaft.

7. A method of coupling a bone implant to a bone augment material comprising:

preparing a second interface surface of the bone augment material to receive a first interface surface of the bone implant, wherein:

the bone implant comprises:

a shaft comprising:

a proximal end;

a distal end; and a longitudinal axis; and a helical thread disposed about the shaft along the longitudinal axis between the proximal end and the distal end of the shaft, wherein the helical thread comprises a concave undercut surface on a first side of the helical thread defining at least a portion of the first interface surface of the bone implant and a convex undercut surface on a second side of the helical thread; and the bone augment material comprises a convex surface shaped to receive the concave undercut surface of the helical thread, the convex surface defining at least a portion of the second interface surface of the bone augment material;

engaging the concave undercut surface of the helical thread with the convex surface of the bone augment material; and coupling at least a portion of the first interface surface of the bone implant with the at least a portion of the second interface surface of the bone augment material to couple the bone implant to the bone augment material.

8. The method of claim 7, wherein preparing the second interface surface of the bone augment material to receive the first interface surface of the bone implant comprises:

coupling the bone augment material to a bone of a patient;

inserting the bone implant into the bone augment material; and curing the bone augment material about the bone implant.

9. The method of claim 7, wherein preparing the second interface surface of the bone augment material to receive the first interface surface of the bone implant comprises:

coupling the bone augment material to a bone of a patient;

inserting a thread-forming instrument into the bone augment material;

curing the bone augment material about the thread-forming instrument; and removing the thread-forming instrument from the bone augment material.

10. The method of claim 7, wherein preparing the second interface surface of the bone augment material to receive the first interface surface of the bone implant comprises:

molding the bone augment material around the bone implant.

11. The method of claim 10, wherein the bone augment material is molded around the bone implant in situ.

12. The method of claim 7, wherein:

the concave undercut surface on the first side of the helical thread comprises:

a first undercut surface; and a second undercut surface; and the convex undercut surface on the second side of the helical thread comprises:

a third undercut surface;

wherein:

the first undercut surface and the third undercut surface are angled toward one of the proximal end and the distal end of the shaft; and the second undercut surface is angled toward the other one of the proximal end and the distal end of the shaft.

13. A method of coupling a bone implant to a bone augment material comprising:

coupling the bone augment material within an untapped bone void formed within a bone of a patient;

rotating a thread-forming tool and moving the thread-forming tool distally into the bone augment material to form a helical bone thread in the bone augment material, wherein the thread-forming tool is separate from the bone implant; and coupling the bone implant to the helical bone thread formed in the bone augment material, wherein:

the bone implant comprises:

a shaft comprising:

a proximal end;

a distal end; and a longitudinal axis; and a helical thread disposed about the shaft along the longitudinal axis between the proximal end and the distal end of the shaft, wherein the helical thread comprises a concave undercut surface, wherein the helical bone thread formed in the bone augment material comprises a convex surface shaped to engage the concave undercut surface of the bone implant to couple the bone implant to the bone augment material.

14. The method of claim 13, wherein the bone augment material comprises at least one of:

a bone cement;

a natural bone graft material; and an artificial bone graft material.

15. The method of claim 13, wherein coupling the bone augment material to the bone of the patient further comprises:

pressing the bone augment material into the untapped bone void formed within the bone of the patient.

16. The method of claim 13, wherein coupling the bone augment material to the bone of the patient further comprises:

injecting the bone augment material into the untapped bone void formed within the bone of the patient, wherein the bone augment material comprises an injectable viscous fluid.

17. The method of claim 16, further comprising:

curing the bone augment material after injection to harden the bone augment material placed within the untapped bone void.

18. The method of claim 13, wherein forming the helical bone thread in the bone augment material further comprises tapping the helical bone thread into the bone augment material with a tapping tool.

19. The method of claim 13, wherein the concave under-cut surface of the helical thread is angled towards one of the proximal end and the distal end of the shaft.

\* \* \* \* \*